(12) United States Patent
Chan et al.

(10) Patent No.: US 12,133,556 B2
(45) Date of Patent: Nov. 5, 2024

(54) AEROSOL-GENERATING DEVICE HAVING A HEAT CONDUCTIVE ASSEMBLY FOR HEAT DISSIPATION

(71) Applicant: Philip Morris Products S.A., Neuchatel (CH)

(72) Inventors: Teck Yan Chan, Singapore (SG); Soon Leong Chew, Singapore (SG)

(73) Assignee: Philip Morris Products S.A., Neuchatel (CH)

( * ) Notice: Subject to any disclaimer, the term of this patent is extended or adjusted under 35 U.S.C. 154(b) by 391 days.

(21) Appl. No.: 17/616,331

(22) PCT Filed: May 21, 2020

(86) PCT No.: PCT/EP2020/064236
§ 371 (c)(1),
(2) Date: Dec. 3, 2021

(87) PCT Pub. No.: WO2020/244929
PCT Pub. Date: Dec. 10, 2020

(65) Prior Publication Data
US 2022/0338544 A1    Oct. 27, 2022

(30) Foreign Application Priority Data
Jun. 5, 2019   (EP) ..................................... 19178525

(51) Int. Cl.
*A24F 40/465* (2020.01)
*A24F 40/60* (2020.01)

(52) U.S. Cl.
CPC ............ *A24F 40/465* (2020.01); *A24F 40/60* (2020.01)

(58) Field of Classification Search
CPC ............................... A24F 40/465; A24F 40/60
(Continued)

(56) References Cited

U.S. PATENT DOCUMENTS 7,724,540 B1 *   5/2010   Salinas Fox ........... H05K 7/142
                                                        361/742
10,028,535 B2 *  7/2018   Mironov ............... H05B 1/0244
(Continued)

FOREIGN PATENT DOCUMENTS

CA       3 097 716 A1    3/2017
CA       3 079 808 A1    5/2019
(Continued)

OTHER PUBLICATIONS

Combined Chinese Office Action and Search Report issued Dec. 17, 2023 in Chinese Patent Application No. 202080034538.8 (with English Translation), 12 pages.
(Continued)

*Primary Examiner* — Neil Abrams
(74) *Attorney, Agent, or Firm* — Oblon, McClelland, Maier & Neustadt, L.L.P.

(57) ABSTRACT

An aerosol-generating device is provided, including: an aerosol generator configured to generate an aerosol from an aerosol-forming substrate; a power supply; a first circuit board including a control circuit configured to control a supply of power from the power supply to the aerosol generator; a heat conductive assembly including a first end in thermal contact with the first circuit board and a second end spaced apart from the first circuit board; and a second circuit board, the first end of the heat conductive assembly being in thermal contact with the second circuit board, the second circuit board at least partially overlies the first circuit board, the second circuit board being spaced apart from the first circuit board, and the first end of the heat conductive assembly being positioned between the first circuit board and the second circuit board.

13 Claims, 6 Drawing Sheets

(58) Field of Classification Search
USPC .......................................................... 131/329
See application file for complete search history.

(56) References Cited

U.S. PATENT DOCUMENTS

| | | | |
|---|---|---|---|
| 11,896,051 B2* | 2/2024 | Taurino | A24F 40/57 |
| 2016/0255879 A1* | 9/2016 | Paprocki | A24F 40/46 |
| 2017/0027233 A1 | 2/2017 | Mironov | |
| 2017/0094998 A1 | 4/2017 | Bernauer et al. | |
| 2018/0173281 A1* | 6/2018 | Lin | H01L 23/4006 |
| 2018/0177958 A1 | 6/2018 | Wilder et al. | |
| 2018/0271153 A1 | 9/2018 | John et al. | |
| 2020/0046031 A1 | 2/2020 | Bernauer et al. | |
| 2020/0163386 A1 | 5/2020 | Courbat et al. | |
| 2021/0137167 A1* | 5/2021 | Aoun | H05B 6/362 |
| 2022/0183376 A1* | 6/2022 | Blandino | H05B 6/105 |
| 2022/0202088 A1* | 6/2022 | Bouchuiguir | A24F 40/46 |
| 2022/0338544 A1* | 10/2022 | Chan | A61M 11/042 |
| 2023/0110163 A1* | 4/2023 | Yoon | A24F 40/40 131/328 |
| 2023/0329335 A1* | 10/2023 | Yamaguchi | F28F 13/003 |
| 2023/0346029 A1* | 11/2023 | Kim | H05B 6/105 |

FOREIGN PATENT DOCUMENTS

| | | |
|---|---|---|
| CN | 202949017 U | 5/2013 |
| CN | 106455712 A | 2/2017 |
| CN | 106535680 A | 3/2017 |
| CN | 109152423 A | 1/2019 |
| JP | 2017-513463 A | 6/2017 |
| JP | 2017-516269 A | 6/2017 |
| JP | 2019-033752 A | 3/2019 |
| KZ | 32912 B | 6/2018 |
| RU | 2611 487 C2 | 2/2017 |
| RU | 2 653 467 C2 | 5/2018 |
| WO | WO 2015/139985 A1 | 9/2015 |
| WO | WO 2015/177043 A1 | 11/2015 |
| WO | WO 2018/119031 A1 | 6/2018 |
| WO | WO 2019/002329 A1 | 1/2019 |
| WO | WO 2020/216762 A1 | 10/2020 |
| WO | WO 2020/229465 A1 | 11/2020 |
| WO | WO 2020/245127 A1 | 12/2020 |

OTHER PUBLICATIONS

International Search Report and Written Opinion issued on Jul. 21, 2020 in PCT/EP2020/064236 filed May 21, 2020, 11 pages.
Extended European Search Report issued Oct. 2, 2019 in European Patent Application No. 19178525.2, 8 pages.
Combined Russian Decision to Grant and Search Report issued Sep. 1, 2023 in Russian Patent Application No. 2021133024/03 (with English Translation), 18 pages.
Japanese Office Action mailed on Jun. 3, 2024 issued in Japanese Patent Application No. 2021-571779, with English Translation, total 4 pages (citing documents 15-17, therein).

* cited by examiner

Figure 8

AEROSOL-GENERATING DEVICE HAVING A HEAT CONDUCTIVE ASSEMBLY FOR HEAT DISSIPATION

CROSS-REFERENCE TO RELATED APPLICATIONS

This application is a U.S. national stage application of PCT/EP2020/064236, filed on May 21, 2020, which is based upon and claims the benefit of priority under 35 U.S.C. § 119 from European patent application no. 19178525.2, filed Jun. 5, 2019, the entire contents of each of which are incorporated herein by reference.

TECHNICAL FIELD

The present invention relates to an aerosol-generating device comprising a heat conductive assembly.

DESCRIPTION OF THE RELATED ART

Aerosol-generating systems in which an aerosol-forming substrate, such as a tobacco containing substrate, is heated rather than combusted are known in the art. The aim of such aerosol-generating systems is to reduce known harmful smoke constituents produced by the combustion and pyrolytic degradation of tobacco in conventional cigarettes. Typically in such aerosol-generating systems, an aerosol is generated by the transfer of energy from an aerosol generator of an aerosol-generating device to an aerosol-forming substrate or material in an aerosol-generating article that is physically separate to the aerosol-generating device. For example, the aerosol generator may be an electric heater and an aerosol may be generated by the transfer of heat from the electric heater to an aerosol-forming substrate. The aerosol-generating article may be located within, around or downstream of the electric heater. During use, volatile compounds are released from the aerosol-forming substrate by heat transfer from the electric heater to the aerosol-forming substrate and entrained in air drawn through the aerosol-generating article. As the released compounds cool, they condense to form an aerosol that may be inhaled by a consumer.

During use of such aerosol-generating devices, the control circuit for controlling a supply of power to the electric heater typically generate a significant amount of heat. Dissipation of the heat generated by the control electronics is necessary to prevent damage to the control circuit. However, the small size of typical aerosol-generating devices combined with the need for a user to hold the device during use makes such dissipation of excess heat difficult.

It would be describable to provide an aerosol-generating device comprising an aerosol generator and a control circuit that facilitates the dissipation of excess heat generated by the control circuit.

SUMMARY

According to the present disclosure, there is provided an aerosol-generating device. The aerosol-generating device may comprise an aerosol generator. The aerosol-generator may be for generating an aerosol from an aerosol-forming substrate. The aerosol-generating device may comprise a power supply. The aerosol-generating device may comprise a circuit board. The circuit board may comprise a control circuit. The control circuit may be for controlling a supply of power from the power supply to the aerosol generator. The circuit board and the power supply may be arranged for the transfer of heat from the circuit board to the power supply.

According to the present disclosure, there is provided an aerosol-generating device comprising an aerosol generator for generating an aerosol from an aerosol-forming substrate, a power supply, and a circuit board comprising a control circuit for controlling a supply of power from the power supply to the aerosol generator. The circuit board and the power supply are arranged for the transfer of heat from the circuit board to the power supply.

BRIEF DESCRIPTION OF THE DRAWINGS

Embodiments of the present invention are described below, by way of example only, with reference to the accompanying drawings in which.

DETAILED DESCRIPTION

Preferably, the circuit board and the power supply are arranged for the conductive transfer of heat from the circuit board to the power supply.

The circuit board may directly contact the power supply. Advantageously, direct contact between the circuit board and the power supply may facilitate direct conductive transfer of heat from the circuit board to the power supply.

The circuit board and the power supply may be arranged for indirect conductive transfer of heat from the circuit board to the power supply. In other words, the aerosol-generating device may comprise at least one additional element arranged for the conductive transfer of heat from the circuit board to the power supply by the at least one additional element. Advantageously, the at least one additional element may provide conductive transfer of heat from the circuit board to the power supply while also facilitating a desired orientation and position of the circuit board with respect to the power supply. The desired orientation and position of the circuit board relative to the power supply may accommodate at least one of a desired size and a desired shape of the aerosol-generating device.

The at least one additional element may comprise a heat conductive assembly. The heat conductive assembly may comprise a first end in thermal contact with the circuit board. The heat conductive assembly may comprise a second end spaced apart from the circuit board.

According to the present disclosure, there is provided an aerosol-generating device. The aerosol-generating device may comprise an aerosol generator. The aerosol generator may be for generating an aerosol from an aerosol-forming substrate. The aerosol-generating device may comprise a power supply. The aerosol-generating device may comprise a circuit board. The circuit board may comprise a control circuit. The control circuit may be for controlling a supply of power from the power supply to the aerosol generator. The aerosol-generating device may comprise a heat conductive assembly. The heat conductive assembly may comprise a first end in thermal contact with the circuit board. The heat conductive assembly may comprise a second end spaced apart from the circuit board.

According to the present disclosure there is provided an aerosol-generating device comprising an aerosol generator for generating an aerosol from an aerosol-forming substrate, a power supply, and a circuit board comprising a control circuit for controlling a supply of power from the power supply to the aerosol generator. The aerosol-generating device also comprises a heat conductive assembly comprising a first end in thermal contact with the circuit board and a second end spaced apart from the circuit board.

Advantageously, the heat conductive assembly conducts excess heat away from the circuit board and towards the second end of the heat conductive assembly. Advantageously, the heat conductive assembly provides at least some control over the location to which excess heat from the circuit board is transferred. Advantageously, the second end of the heat conductive assembly may be positioned at a location in which it is desirable to dissipate excess heat generated by the control circuit.

As used herein, the term "aerosol-generating device" refers to a device that interacts with an aerosol-forming substrate to generate an aerosol.

As used herein, the term "aerosol-forming substrate" refers to a substrate capable of releasing volatile compounds that can form an aerosol. Such volatile compounds may be released by heating the aerosol-forming substrate. An aerosol-forming substrate may form part of an aerosol-generating article.

As used herein, the term "aerosol-generating article" refers to an article comprising an aerosol-forming substrate that is capable of releasing volatile compounds that can form an aerosol. For example, an aerosol-generating article may be an article that generates an aerosol that is directly inhalable by the user drawing or puffing on a mouthpiece at a proximal or user-end of the system. An aerosol-generating article may be disposable. An article comprising an aerosol-forming substrate comprising tobacco may be referred to as a tobacco stick.

As used herein, the term "aerosol-generating system" refers to the combination of an aerosol-generating device and an aerosol-generating article. In the aerosol-generating system, the aerosol-generating article and the aerosol-generating device cooperate to generate an aerosol.

Preferably, the second end of the heat conductive assembly is in thermal contact with the power supply.

Advantageously, during use, there may be a high thermal gradient between the circuit board and the power supply. Advantageously, the high thermal gradient and the thermal contact between the second end of the heat conductive assembly and the power supply may increase or maximise the rate of transfer of heat away from the circuit board by the heat conductive assembly.

Advantageously, transferring heat from the circuit board to the power supply may facilitate use of the aerosol-generating device in cold ambient temperatures. For example, at temperatures of about 5 degrees Celsius and less, the performance of some power supplies may be diminished. Therefore, transferring heat from the circuit board to the power supply may advantageously raise the temperature of the power supply above ambient temperature. Advantageously, raising the temperature of the power supply above ambient temperature may maintain or improve the performance of the power supply.

Preferably, the heat conductive assembly comprises a heat conductive frame defining the second end of the heat conductive assembly. Preferably, the power supply is positioned at least partially within the heat conductive frame.

Advantageously, providing the heat conductive assembly with a heat conductive frame may facilitate positioning of the power supply and the heat conductive assembly relative to each other during assembly of the aerosol-generating device.

Advantageously, positioning the power supply within the heat conductive frame may facilitate the transfer of heat from the second end of the heat conductive assembly to the power supply.

An aerosol-generating device according to any preceding claim, wherein the heat conductive assembly comprises at least one transverse member at the first end of the heat conductive assembly, and wherein a portion of the at least one transverse member is positioned within a slot defined by the circuit board.

Advantageously, providing the heat conductive assembly with at least one transverse member positioned within a slot defined by the circuit board may facilitate thermal contact between the circuit board and the first end of the heat conductive assembly.

Advantageously, providing the heat conductive assembly with at least one transverse member positioned within a slot defined by the circuit board may help to retain the first end of the heat conductive assembly in thermal contact with the circuit board. Advantageously, the combination of the at least one transverse member and the slot may eliminate the need to solder or adhere the first end of the heat conductive assembly to the circuit board. Advantageously, eliminate the need to solder or adhere the first end of the heat conductive assembly to the circuit board may simplify at least one of the manufacture and repair of the aerosol-generating device.

Advantageously, providing the heat conductive assembly with at least one transverse member positioned within a slot defined by the circuit board may facilitate positioning of the circuit board and the heat conductive assembly relative to each other during assembly of the aerosol-generating device.

Preferably, the at least one transverse member is received within the slot by an interference fit. Advantageously, the interference fit may facilitate thermal contact between the at least one transverse member and the circuit board. Advantageously, the interference fit may facilitate retention of the at least one transverse member within the slot.

The at least one transverse member may comprise a plurality of transverse members. The circuit board may define a plurality of slots, wherein each of the transverse member is received within a different slot defined by the circuit board.

Advantageously, providing a plurality of transverse members may increase the rate of heat transfer from the circuit board to the first end of the heat conductive assembly.

Advantageously, providing a plurality of transverse members may facilitate thermal contact between the first end of the heat conductive assembly and a plurality of locations on the circuit board. Advantageously, the plurality of locations may be selected to provide a desired profile of heat transfer from the circuit board to the first end of the heat conductive assembly. For example, where the heat generated by the control circuit results in a non-uniform temperature distribution across at least a portion of the circuit board during use, the plurality of transverse members may be positioned to accommodate the non-uniform temperature profile.

Advantageously, providing a plurality of transverse members may further facilitate positioning of the circuit board and the heat conductive assembly relative to each other during assembly of the aerosol-generating device.

The slot defined by the circuit board may be a first slot and the circuit board define a second slot. The at least one transverse member may comprise a first transverse member having a first portion positioned within the first slot and a second transverse member having a second portion positioned within the second slot.

The slot defined by the circuit board may extend through the circuit board from a first side of the circuit board to a second side of the circuit board. The at least one transverse member may extend through the slot so that the at least one transverse member protrudes from the first side of the circuit board and from the second side of the circuit board. In other words, the at least one transverse member may extend entirely through a thickness of the circuit board.

Advantageously, a transverse member extending entirely through a thickness of the circuit board may increase or maximise the thermal contact area between the at least one transverse member and the circuit board.

The heat conductive assembly may comprise at least one longitudinal arm extending between the at least one transverse member and the heat conductive frame.

Advantageously, the at least one longitudinal arm may facilitate the transfer of heat from the at least one transverse member at the first end of the heat conductive assembly to the heat conductive frame at the second end of the heat conductive assembly.

Advantageously, the at least one longitudinal arm may be flexible. Advantageously, at least one flexible longitudinal arm may facilitate positioning of the at least one transverse member in the slot during assembly of the aerosol-generating device.

In embodiments in which the heat conductive assembly comprises a plurality of transverse members, preferably the heat conductive assembly comprises a plurality of longitudinal arms. Preferably, each longitudinal arm extends between one of the transverse members and the heat conductive frame.

In embodiments in which the heat conductive assembly comprises a first transverse member and a second transverse member, preferably the at least one longitudinal arm comprises a first longitudinal arm extending between the first transverse member and the heat conductive frame, and a second longitudinal arm extending between the second transverse member and the heat conductive frame.

The circuit board may be a first circuit board and the aerosol-generating device may further comprise a second circuit board. Preferably, the first end of the heat conductive assembly is in thermal contact with the first circuit board and the second circuit board.

Advantageously, the first and second circuit boards may facilitate providing the aerosol-generating device with at least one of a desired size and a desired shape. For example, the first and second circuit boards may facilitate an aerosol-generating device having a shorter length when compared to an aerosol-generating device comprising a single circuit board.

Advantageously, the first and second circuit boards may facilitate the separation of two or more electrical components of the aerosol-generating device. Advantageously, providing a first set of electrical components on the first circuit board and a second set of electrical components on the second circuit board may facilitate thermal separation of the first and second sets of electrical components.

Preferably, the second circuit board at least partially overlies the first circuit board. Advantageously, at least partially overlying the first and second circuit boards may facilitate thermal contact of the first end of the heat conductive assembly with both the first and second circuit boards.

Preferably, the first circuit board is spaced apart from the second circuit board. Preferably, the first end of the heat conductive assembly is at positioned between the first circuit board and the second circuit board. Advantageously, positioning the first end of the heat conductive assembly between the first and second circuit boards may facilitate thermal contact of the first end of the heat conductive assembly with both the first and second circuit boards.

Preferably, the control circuit for controlling the supply of power from the power supply to the aerosol generator is provided on the first circuit board. Preferably, the aerosol generator is electrically connected to the first circuit board.

As used herein, the term "electrically connected" refers to a connection by means of an electrically conductive path.

Preferably, the power supply is electrically connected to at least one of the first circuit board and the second circuit board. The power supply may be electrically connected to both the first circuit board and the second circuit board.

Preferably, the aerosol-generating device comprises one or more additional electrical components. Preferably, the one or more additional electrical components comprises at least one of a charging connector, a feedback device, a user input device, and an airflow sensor. Preferably, at least one of the one or more additional electrical components is positioned on the second circuit board or electrically connected to the second circuit board.

Preferably, the aerosol-generating device comprises a device controller configured to control the operation of the aerosol-generating device. Preferably, the device controller is provided on the second circuit board. Preferably, the device controller is in electrical communication with the one or more additional electrical components. Preferably, the device controller is electrically connected to the power supply. Preferably, the device controller is in electrical communication with the control circuit for controlling the supply of power from the power supply to the aerosol generator. Preferably, the first circuit board is electrically connected to the second circuit board. Preferably, the electrical connection between the first circuit board and the second circuit board provides the electrical communication between the device controller and the control circuit for controlling the supply of power from the power supply to the aerosol generator.

In embodiments in which the heat conductive assembly comprises at least one transverse member, preferably at least a portion of the at least one transverse member is positioned within a slot defined by the second circuit board. Advantageously, positioning the at least one transverse member within slots defined by the first and second circuit boards may facilitates the transfer of heat away from both the first and second circuit boards by the heat conductive assembly.

In embodiments in which the at least one transverse member comprises a plurality of transverse member, at least one of the transverse members may be received within the slot defined by the first circuit board and the slot defined by the second circuit board. At least one of the transverse member may comprise a first end received within the slot defined by the first circuit board and a second end received within the slot defined by the second circuit board.

Advantageously, providing at least one transverse member that is received within slots defined by the first and second circuit boards may reduce or minimise the number of transverse members required to provide a desired thermal contact between the first end of the heat conductive assembly and each of the first and second circuit boards.

Preferably, at least one of the transverse members is in thermal contact with the first circuit board only. Advantageously, providing a transverse member that is in thermal contact with the first circuit board only may facilitate a higher rate of transfer of heat away from the first circuit board by the heat conductive assembly compared to a rate of transfer of heat away from the second circuit board by the heat conductive assembly. Advantageously, a higher rate of transfer of heat away from the first circuit board by the heat conductive assembly may accommodate the significant amount of heat generated by the control circuit for controlling a supply of power from the power supply to the aerosol generator.

As described herein, the heat conductive assembly may comprise a first transverse member positioned within a first slot defined by the first circuit board and a second transverse member positioned within a second slot defined by the first circuit board. Preferably, the second circuit board defines a third slot, wherein the second transverse member has a third portion positioned within the third slot. Preferably, the first transverse member is in thermal contact with the first circuit board only.

The heat conductive assembly is formed from a thermally conductive material. Preferably, the thermally conductive material has a thermal conductivity of at least about 190 watts per meter kelvin at 23 degrees Celsius and a relative humidity of 50 percent as measured using the modified transient plane source (MTPS) method.

Suitable thermally conductive materials may comprise a metal. The heat conductive assembly may be metallic. Suitable metals include aluminium, copper, iron, gold, zinc or any suitable alloy of such metals. Suitable alloys include some stainless steels and some copper alloys, such as brass, copper and nickel alloys, copper beryllium alloys, and phosphor bronze.

Preferably, the heat conductive assembly is formed from brass. Advantageously, brass may be sufficiently malleable to facilitate forming the heat conductive assembly with a required shape. Advantageously, a heat conductive assembly formed from brass may be sufficiently resilient to facilitate the retention of one or more components of the aerosol-generating device by the heat conductive assembly. For example, in embodiments in which the heat conductive assembly comprises a heat conductive frame, a brass heat conductive assembly may be sufficiently resilient to facilitate retention of the power supply within the heat conductive frame.

The aerosol-generating device may comprise an inner housing. Advantageously, the inner housing may support one or more components of the aerosol-generating device.

The circuit board may be secured to the inner housing. The circuit board may be secured to the housing by an interference fit between a portion of the circuit board and the inner housing. In embodiments in which the aerosol-generating device comprises a first circuit board and a second circuit board, the first and second circuit boards may be secured to the inner housing.

Preferably, the power supply is positioned within the inner housing.

Preferably, the second end of the heat conductive assembly is in thermal contact with the inner housing. Advantageously, thermal contact between the heat conductive assembly and the inner housing may facilitate dissipation of heat from the circuit board into the inner housing by the heat conductive assembly.

In embodiments in which the heat conductive assembly comprises a heat conductive frame, preferably the heat conductive frame is in thermal contact with the inner housing.

At least a part of the second end of the heat conductive assembly may overlie a portion of the inner housing.

Preferably, a portion of the inner housing is overmolded over at least a part of the second end of the heat conductive assembly. Advantageously, overmolding a portion of the inner housing over at least a part of the second end of the heat conductive assembly may embed at least a part of the second end of the heat conductive assembly within the material forming the inner housing. Advantageously, embedding at least a part of the heat conductive assembly within the material forming the inner housing may facilitate the transfer of heat from the second end of the heat conductive assembly to the inner housing.

In embodiments in which the second end of the heat conductive assembly comprises a heat conductive frame, preferably a portion of the inner housing is overmolded over at least a part of the heat conductive frame.

Preferably, the inner housing is formed from a material that is suitable for molding over the heat conductive assembly. The inner housing may be formed from a polymer material. The inner housing may be formed from a moldable polymer. Preferably, the inner housing is formed from a material that is suitable for use in a molding process, such as injection moulding. Suitable polymer materials include thermoplastics materials and thermosetting polymers. Suitable polymer materials include: polyphthalamide (PPA), polycarbonate (PC), a blend of polycarbonate and acrylonitrile butadiene styrene (PC-ABS), polyphenylsulfone (PPSU), polyetheretherketone (PEEK), polypropylene (PP), polyethylene (PE), polyimide (PI), thermoplastic polyimide (TPI), polyamidimide (PAI), and polyetherimide (PEI). The polymer material may be a composite polymer material. The composite polymer material may comprise other materials. The composite polymer material may comprise at least one fibrous filler material. The at least one fibrous filler material may comprise at least one of carbon fibres and glass fibres.

The control circuit for controlling a supply of power from the power supply to the aerosol generator may comprise at least one of a microprocessor, a microcontroller, and an application specific integrated chip (ASIC).

In embodiments in which the aerosol-generating device comprises a device controller, the device controller may comprise at least one of a microprocessor, a microcontroller, and an application specific integrated chip (ASIC).

The power supply may be a DC power supply. In preferred embodiments, the power supply is a battery. The power supply may be a nickel-metal hydride battery, a nickel cadmium battery, or a lithium based battery, for example a lithium-cobalt, a lithium-iron-phosphate or a lithium-polymer battery. The power supply may be another form of charge storage device, such as a capacitor. The power supply may require recharging and may have a capacity that allows for the storage of enough energy for one or more user operations, for example one or more aerosol-generating experiences. For example, the power supply may have sufficient capacity to allow for continuous heating of an aerosol-forming substrate for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heater.

Preferably, the aerosol-generating device comprises a cavity for receiving an aerosol-forming substrate. In embodiments in which the aerosol-generating device comprises an inner housing, the inner housing may at least partially define the cavity.

Preferably, the aerosol-generating device comprises an outer housing. In embodiments in which the aerosol-generating device comprises a cavity for receiving an aerosol-forming substrate, the outer housing may at least partially define the cavity.

The housing may be elongate. The housing may have a cylindrical shape. The housing may comprise any suitable material or combination of materials. Suitable materials include metals, alloys, plastics, and composite materials containing at least one of a metal, an alloy and a plastic. Suitable material include thermoplastics that are suitable for food or pharmaceutical applications. Suitable thermoplastics include polypropylene, polyetheretherketone (PEEK) and polyethylene.

Preferably, the aerosol-generating device is portable. The aerosol-generating device may have a length of between about 70 millimetres and about 120 millimetres. Preferably, the aerosol-generating device is a handheld device. In other words, the aerosol-generating device may be sized and shaped to be held in the hand of a user.

The aerosol generator may comprise an electric heater.

The electric heater may comprise at least one internal heating element. As used herein, the term "internal heating element" refers to a heating element configured to be inserted into an aerosol-forming substrate. The internal heating element may be in the form of at least one of a blade, a pin, and a cone. The internal heating element is preferably configured to be insertable into an aerosol forming substrate. In embodiments in which the aerosol-generating device comprises a cavity for receiving an aerosol-forming substrate, preferably the at least one internal heating element extends into the cavity.

The electric heater may comprise at least one external heating element. As used herein, the term "external heating element" refers to a heating element configured to heat an outer surface of an aerosol-forming substrate. The at least one external heating element is preferably configured to at least partially surround an aerosol forming substrate received by the aerosol-generating device. In embodiments in which the aerosol-generating device comprises a cavity for receiving an aerosol-forming substrate, preferably the at least one external heating element at least partially surrounds the cavity.

The electric heater may comprise at least one internal heating element and at least one external heating element.

In some preferred embodiments, the heater comprises at least one resistive heating element.

The electric heater may comprise a resistive heating element. The resistive heating element may comprise an electrically insulating substrate and one or more electrically conductive tracks or wire provided on the surface of the electrically insulating substrate. The size and shape of the electrically insulating substrate may facilitate insertion of the electric heater into an aerosol-forming substrate. Preferably, the electrically insulating substrate is rigid. The aerosol-generating device may comprise only one resistive heating element. The aerosol-generating device may comprise a plurality of resistive heating elements.

The aerosol generator may comprise a transfer element. The transfer element may be arranged to transfer a liquid aerosol-forming substrate to the electric heater. The transfer element may comprise a capillary wick. Preferably, the electric heater contacts the transfer element. The electric heater may comprise a resistive heating wire. At least a portion of the resistive heating wire may be coiled around the transfer element. The electric heater may comprise a resistive heating mesh.

The aerosol generator may comprise an inductive heating arrangement. The inductive heating arrangement may comprise an inductor coil. Preferably, the control circuit for controlling a supply of power from the power supply to the aerosol generator is configured to provide a high frequency oscillating current to the inductor coil from the power supply. As used herein, the term "high frequency oscillating current" refers to an oscillating current having a frequency of between 500 kilohertz and 30 megahertz. Aerosol-generating device may comprise a DC/AC inverter for converting a DC current supplied by a DC power supply to the oscillating current. The inductor coil may be arranged to generate a high frequency oscillating electromagnetic field on receiving the high frequency oscillating current from the power supply. The inductor coil may be arranged to generate a high frequency oscillating electromagnetic field in a device cavity configured to receive an aerosol-forming substrate. In embodiments in which the aerosol-generating device comprises a cavity for receiving an aerosol-forming substrate, the inductor coil may substantially circumscribe the cavity. The inductor coil may extend at least partially along a length of the cavity.

In embodiments in which the aerosol generator comprises an inductive heating arrangement, the aerosol generator may comprise an inductive heating element. The inductive heating element may be a susceptor element. As used herein, the term "susceptor element" refers to an element comprising a material that is capable of converting electromagnetic energy into heat. When a susceptor element is located in an oscillating electromagnetic field, the susceptor is heated. Heating of the susceptor element may be the result of at least one of hysteresis losses and eddy currents induced in the susceptor element, depending on the electrical and magnetic properties of the susceptor material. In embodiments in which the aerosol-generating device comprises a cavity for receiving an aerosol-forming substrate, a susceptor element may be arranged such that, when an aerosol-forming substrate is received in the cavity, the oscillating electromagnetic field generated by the inductor coil induces a current in the susceptor element, causing the susceptor element to heat the aerosol-forming substrate. The susceptor element may be positioned within the cavity. The aerosol-generating device may comprise only one susceptor element. The aerosol-generating device may comprise a plurality of susceptor elements.

A susceptor element may comprise any suitable material. The susceptor element may be formed from any material that can be inductively heated to a temperature sufficient to release volatile compounds from an aerosol-forming substrate. The susceptor element may comprise a metal or carbon. Suitable materials for the susceptor element include graphite, molybdenum, silicon carbide, stainless steels, niobium, aluminium, nickel, nickel containing compounds, titanium, and composites of metallic materials. The susceptor element may comprise a ferromagnetic material, for example, ferritic iron, a ferromagnetic alloy, such as ferromagnetic steel or stainless steel, ferromagnetic particles, and ferrite.

In embodiments in which the aerosol generator comprises an inductive heating arrangement, the aerosol generator may comprise only an inductor coil. In other words, the aerosol-generating device may comprise no susceptor elements. The aerosol-generating device may receive an aerosol-generating article comprising an aerosol-forming substrate and at least one susceptor element. During use, the oscillating electromagnetic field generated by the inductor coil induces a current in the susceptor element of the aerosol-generating article, causing the susceptor element to heat the aerosol-forming substrate.

The aerosol generator may comprise an element arranged to oscillate when supplied with power from the power supply. The aerosol generator may comprise a piezoelectric element. The aerosol-generator may comprise at least one nozzle. The piezoelectric element may be arranged to eject droplets of a liquid aerosol-forming substrate through the at least one nozzle. The aerosol generator may comprise a mesh, wherein the mesh defines the at least one nozzle.

The mesh may be arranged to oscillate during use of the aerosol-generating device. An oscillating mesh may be termed an "active mesh". The mesh may be formed from a piezoelectric material. The mesh may be the piezoelectric element. The piezoelectric element may be formed separately from the mesh and arranged to oscillate the mesh during use.

The mesh may be arranged to remain substantially stationary with respect to the oscillating piezoelectric element during use of the aerosol-generating device. A stationary mesh may be termed a "passive mesh". The aerosol generator may comprise a reservoir positioned between the mesh and the piezoelectric element. The reservoir may be arranged to receive a liquid aerosol-forming substrate.

Figure 1:
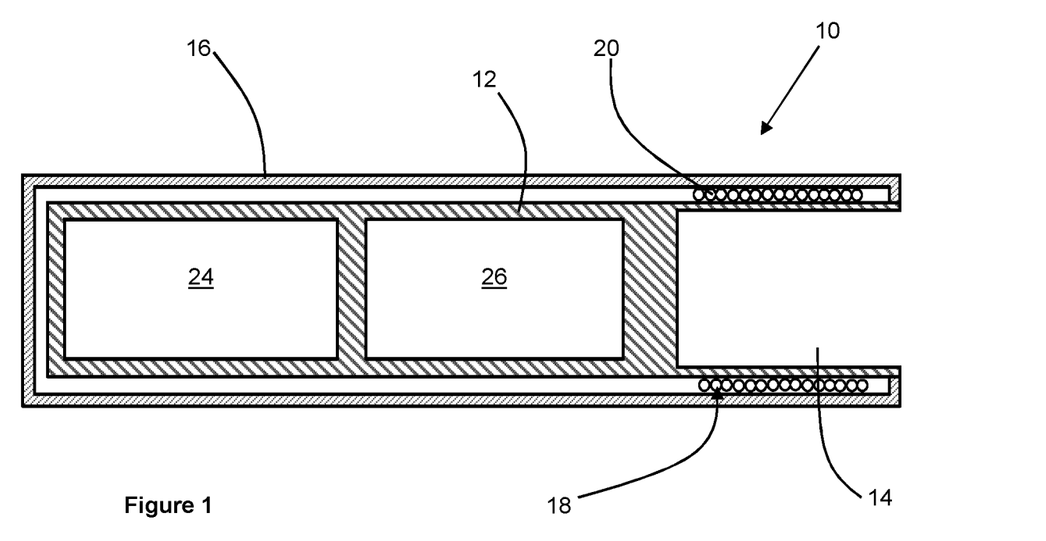
FIG. 1 shows a schematic cross-sectional view of an aerosol-generating device according to a first embodiment of the present invention.

FIG. 1 shows a schematic cross-sectional view of an aerosol-generating device 10 according to a first embodiment of the present invention. The aerosol-generating device 10 comprises an inner housing 12 defining a cavity 14 for receiving an aerosol-forming substrate at a first end of the aerosol-generating device 10. The aerosol-generating device 10 also comprises an outer housing 16 extending around the inner housing 12.

The aerosol-generating device 10 also comprises an aerosol generator 18 comprising an inductive heating arrangement. The inductive heating arrangement comprises an inductor coil 20 surrounding the cavity 14. During use, an aerosol-forming article comprising an aerosol-forming substrate and a susceptor element is inserted into the cavity 14.

A power supply 24 is positioned within the inner housing 12 at a second end of the aerosol-generating device 10. The power supply 24 is a rechargeable battery.

The aerosol-generating device 10 also comprises a number of control components illustrated generally by the box 26 in FIG. 1. The control components and their functional connectivity to each other (illustrated by connecting arrows) are shown in more detail in the schematic illustration in FIG. 2.

Figure 2:
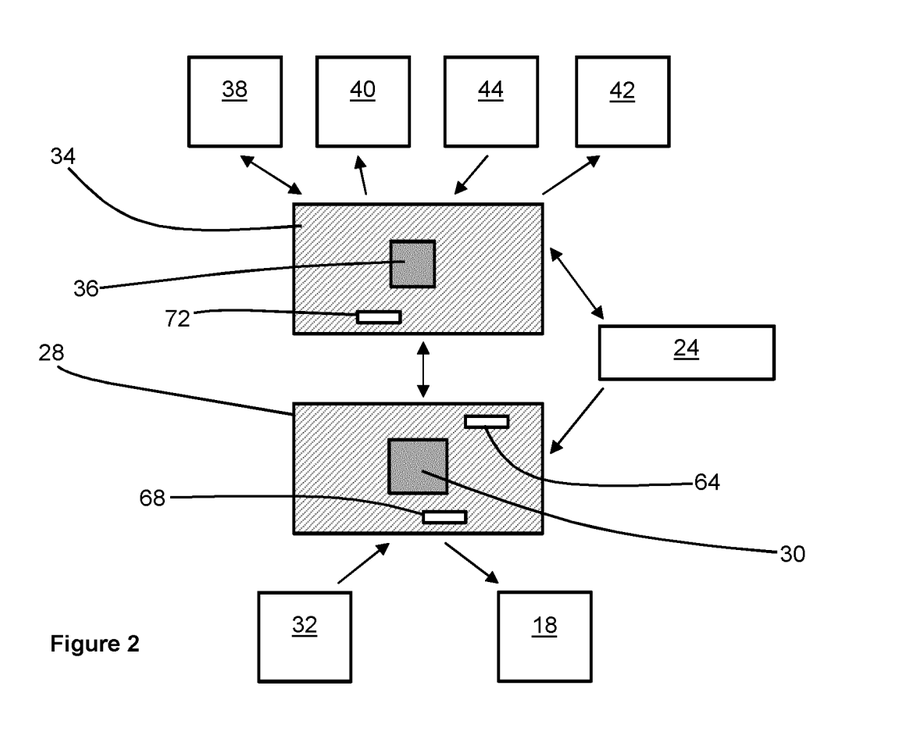
FIG. 2 illustrates the electric connection between electrical components of the aerosol-generating device of FIG. 1.

The aerosol-generating device 10 comprises a first circuit board 28 on which a control circuit 30 is provided. The control circuit 30 is configured to control a supply of power from the power supply 24 to the aerosol generator 18. In particular, the control circuit 30 comprises a DC/AC inverter to convert a DC supply of power from the power supply 24 into an oscillating electrical current that is supplied to the inductor coil 20. During use, the oscillating electrical current in the inductor coil 20 generates a high frequency oscillating electromagnetic field within the cavity 14. The high frequency oscillating electromagnetic field inductively heats the susceptor element of an aerosol-generating article received within the cavity 14, which heats the aerosol-forming substrate of the aerosol-generating article.

A puff sensor 32 is arranged within or in communication with the cavity 14. The puff sensor is arranged to sense when a user is drawing air through the cavity 14 to inhale an aerosol generated by an aerosol-forming substrate received within the cavity 14. The puff sensor 32 comprises a pressure sensor. The puff sensor 32 is electrically connected to the first circuit board 28 to communicate data generated by the puff sensor 32 to the control circuit 30.

The aerosol-generating device 10 also comprises a second circuit board 34 on which a device controller 36 is provided. The device controller 36 communicates with the control circuit 30 to command the control circuit 30 to control the supply of power from the power supply 24 to the aerosol generator 18 or to stop the supply of power from the power supply 24 to the aerosol generator 18. The device controller 36 may also receive data generated by the puff sensor 32 via the control circuit 30.

A charging connector 38 is positioned at the second end of the aerosol-generating device 10 and is electrically connected to the second circuit board 34. The charging connector 38 is configured to receive a supply of power from an external device, such as a main charger or a universal serial bus (USB) charger. The device controller 36 controls the supply of power received by the charging connector 38 for recharging the power supply 24.

Two feedback devices comprising a light emitting diode (LED) module 40 and a vibration motor 42 are electrically connected to the second circuit board 34. The device controller 36 is configured to provide feedback to a user using the two feedback devices. For example, the device controller 36 may control the LED module 40 to provide a status of the power supply 24 to a user. The device controller 36 may control the vibration motor 42 to indicate at least one of the start of a heating cycle and the end of a heating cycle.

A user input device comprising a push button 44 is electrically connected to the second circuit board 34. The push button 44 allows a user to operate the aerosol-generating device by providing one or more signals to the device controller 36. For example, the device controller 36 may be configured to allow a user to use a single button push, or a combination of button pushes, to start a heating cycle, to end a heating cycle, to generate feedback using at least one of the LED module 40 and the vibration motor 42, and to modify a configuration of the aerosol-generating device 10.

Figure 3:
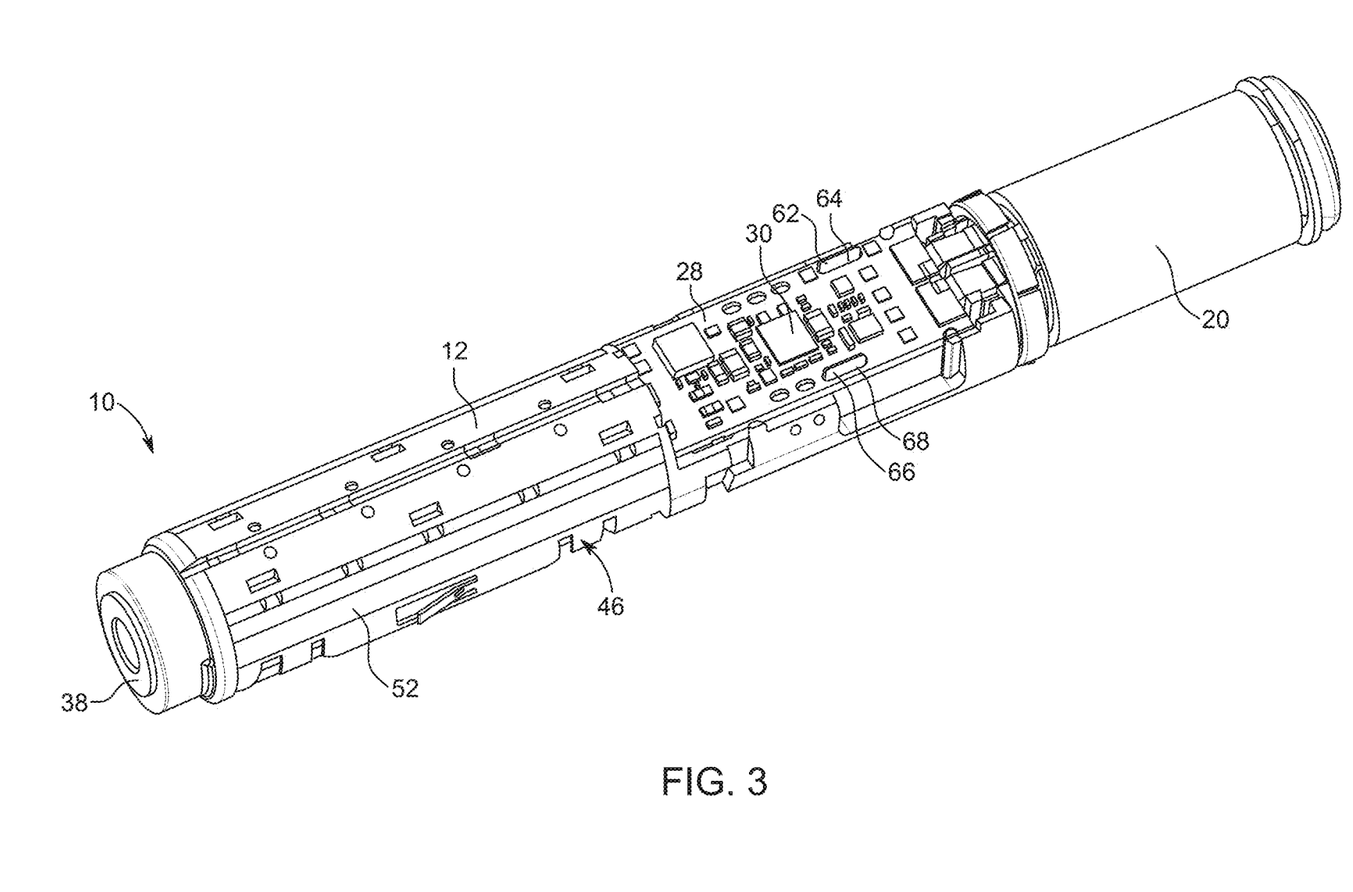
FIG. 3 shows a top perspective view of the aerosol-generating device of FIG. 1 with the outer housing removed.
Figure 4:
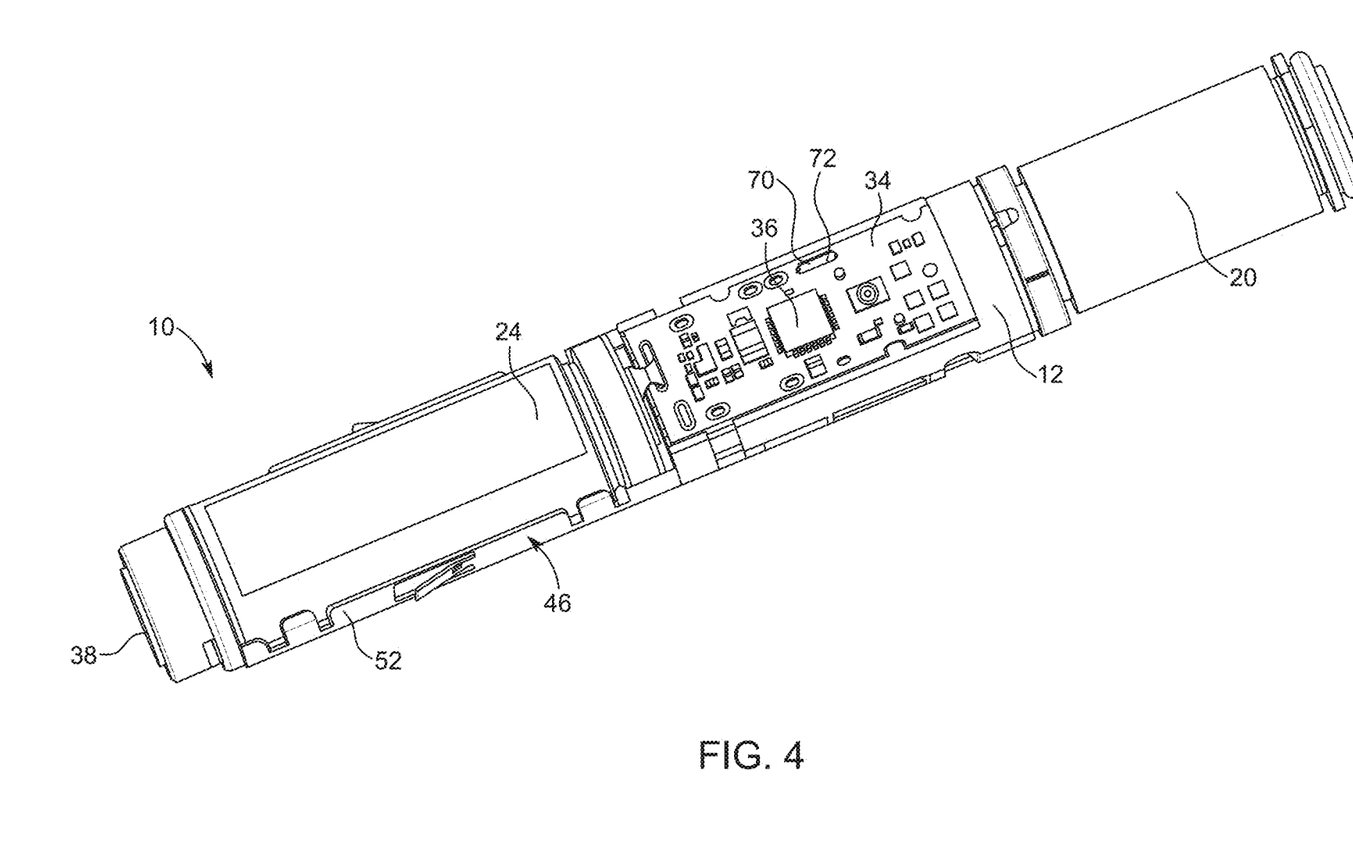
FIG. 4 shows a bottom perspective view of the aerosol-generating device of FIG. 1 with the outer housing removed.

FIGS. 3 and 4 show a top perspective view and a bottom perspective view of the aerosol-generating device 10 with the outer housing 16 removed to show the arrangement of the first and second circuit boards 28, 34 within the aerosol-generating device 10. The first circuit board 28 overlies the second circuit board 34.

During use of the aerosol-generating device 10, electrical components provided on the first and second circuit boards 28, 34, including the control circuit 30 and the device controller 36, generate heat. To dissipate the generated heat from the first and second circuit boards 28, 34 and to prevent thermal damage to the control circuit 30 and the device controller 36, the aerosol-generating device comprises a heat conductive assembly 46. The integration of the heat conductive assembly 46 into the aerosol-generating device 10 is shown in FIGS. 3 and 4. The heat conductive assembly 46 is shown in detail, separate from the aerosol-generating device 10, in FIG. 5.

Figure 5:
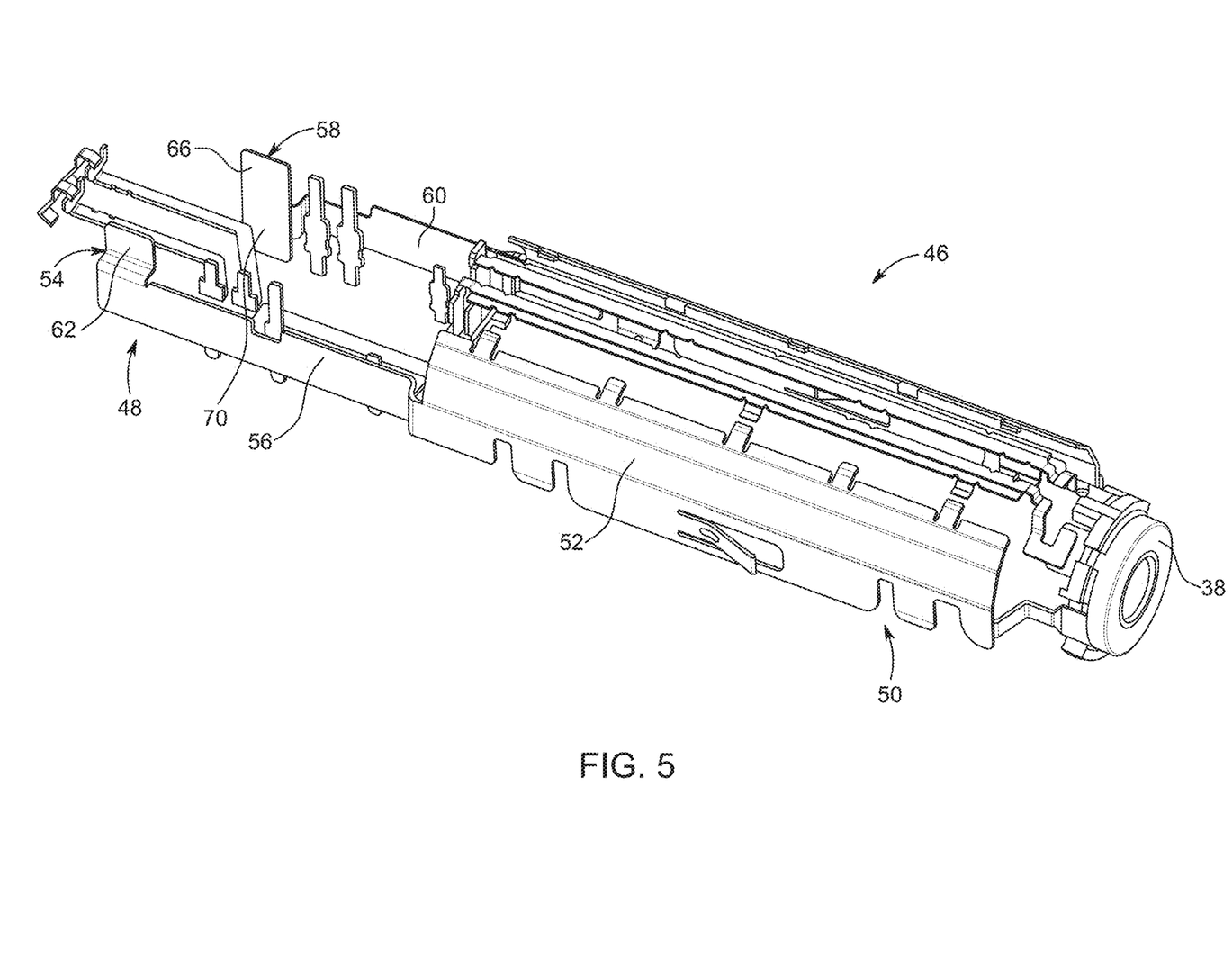
FIG. 5 shows a perspective view of the heat conductive assembly of the aerosol-generating device of FIG. 1.

The heat conductive assembly 46 comprises a first end 48 positioned between the first circuit board 28 and the second circuit board 34, and a second end 50 spaced apart from the first and second circuit boards 28, 34.

The second end 50 of the heat conductive assembly 46 is defined by a heat conductive frame 52 arranged to partially surround the power supply 24 to provide thermal contact between the second end 50 of the heat conductive assembly 46 and the power supply 24. In the assembled aerosol-generating article 10 shown in FIG. 3, the heat conductive frame 52 is partially embedded within the inner housing 12 by overmolding a portion of the inner housing 12 over the heat conductive frame 52 during manufacture of the aerosol-generating device 10.

The first end 48 of the heat conductive assembly 46 comprises a first transverse member 54, a first longitudinal arm 56 extending between the first transverse member 54 and the heat conductive frame 52, a second transverse member 58, and a second longitudinal arm 60 extending between the second transverse member 58 and the heat conductive frame 52.

The first and second transverse members 54, 58 are positioned within slots defined by the first and second circuit boards 28, 34 to provide thermal contact between the first end 48 of the heat conductive assembly 46 and each of the first and second circuit boards 28, 34. The first transverse member 54 comprises a first portion 62 positioned within a first slot 64 defined by the first circuit board 28. The second transverse member 58 comprises a second portion 66 positioned within a second slot 68 defined by the first circuit board 28. The second transverse member 58 also comprises a third portion 70 positioned within a third slot 72 defined by the second circuit board 34.

The thermal contact between the first and second transverse members 54, 58 and the first and second circuit boards 28, 34 facilitates the transfer of heat from the first and second circuit boards 28, 34 into the first end 48 of the heat conductive assembly 46. Heat transferred into the first end 48 of the heat conductive assembly 46 is conducted along the first and second longitudinal arms 56, 60 and into the heat conductive frame 52 where it is dissipated into the power supply 24 and the inner housing 12. The thermal contact between the first and second transverse members 54, 58 and the first circuit board 28 provides a higher rate of heat transfer than the thermal contact between the second circuit board 34 and the second transverse member 58 only. The higher rate of heat transfer accommodates the higher rate of heat generation by the control circuit 30 compared to the device controller 36.

Figure 6:
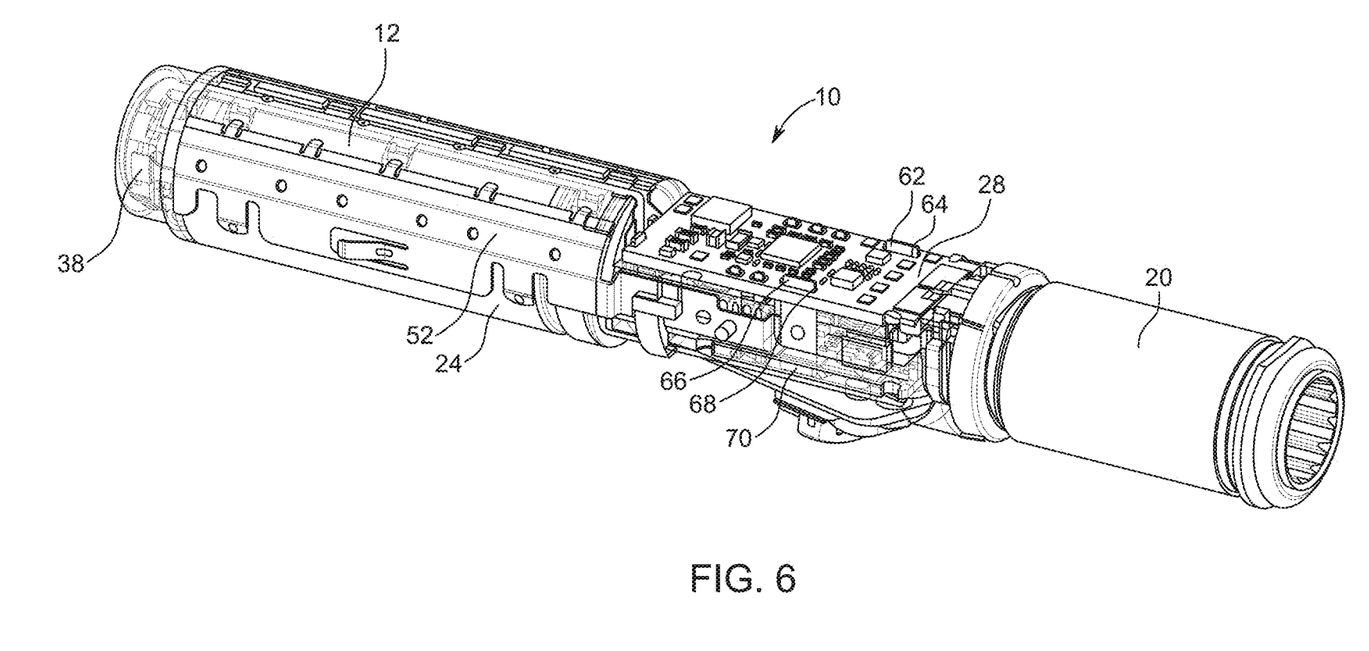
FIG. 6 shows an alternative arrangement of the heat conductive assembly with respect to the inner housing of the aerosol-generating device of FIG. 1.

FIG. 6 shows an alternative arrangement of the heat conductive frame 52 with respect to the inner housing 12. In the embodiment shown in FIG. 6, the heat conductive frame 52 entirely overlies the inner housing 12 and the power supply 24. In other words, the heat conductive frame 52 is not partially embedded within the inner housing 12. Although this arrangement simplifies the assembly of the aerosol-generating device 10, since it does not require overmolding of the inner housing 12 over the heat conductive frame 52, the rate of heat transfer from the heat conductive frame 52 to the inner housing 12 may be reduced.

Figure 7:
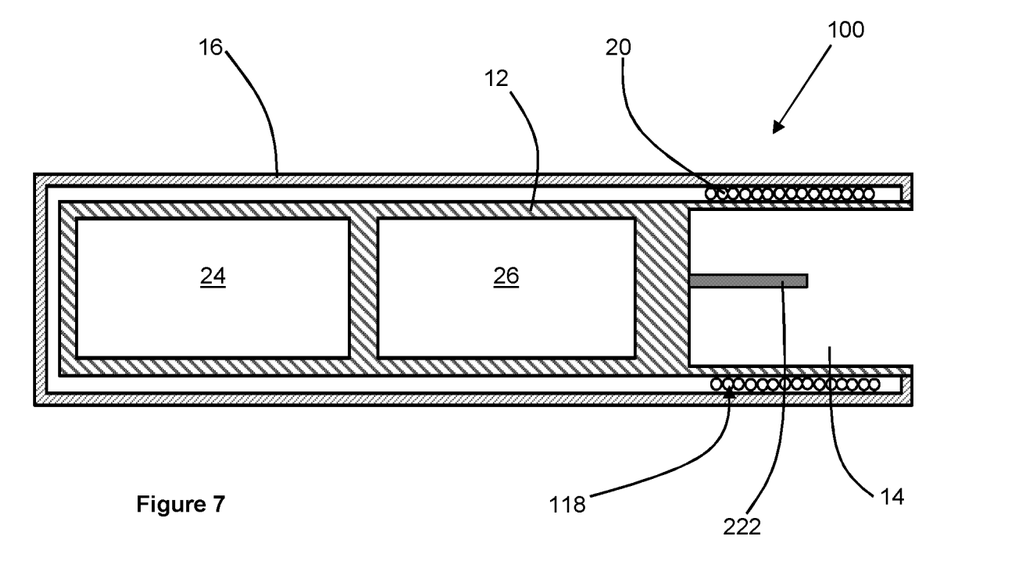
FIG. 7 shows a schematic cross-sectional view of an aerosol-generating device according to a second embodiment of the present invention.

FIG. 7 shows an aerosol-generating device 100 according to a second embodiment of the present invention. The aerosol-generating device 100 is substantially the same as the aerosol-generating device of FIG. 1 and like reference numerals are used to designate like parts.

The aerosol-generating device 100 differs from the aerosol-generating device 10 by the aerosol-generator. Although the aerosol-generating device 100 includes an aerosol-generator 118 comprising an inductor coil 20, the aerosol-generator 118 also comprises a susceptor element 222 extending into the cavity 14. During use, an aerosol-forming substrate is inserted into the cavity 14 so that the susceptor element 222 is received within the aerosol-forming substrate.

The remainder of the aerosol-generating device 100, including the head conductive assembly 46, is identical to the aerosol-generating device 10 of FIG. 1.

Figure 8:
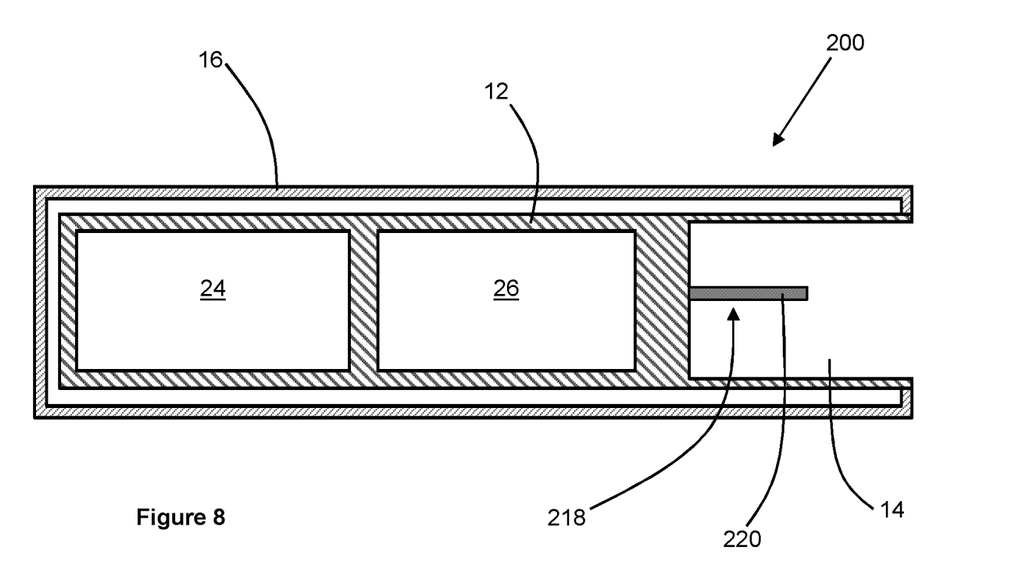
FIG. 8 shows a schematic cross-sectional view of an aerosol-generating device according to a third embodiment of the present invention.

FIG. 8 shows an aerosol-generating device 200 according to a third embodiment of the present invention. The aerosol-generating device 200 is substantially the same as the aerosol-generating device of FIG. 1 and like reference numerals are used to designate like parts.

The aerosol-generating device 200 differs from the aerosol-generating device 10 by the aerosol-generator. Instead of an inductor coil, the aerosol-generator 218 of the aerosol-generating device 200 comprises an electric heater 220 comprising a resistive heating element extending into the cavity 14. During use, an aerosol-forming substrate is inserted into the cavity 14 so that the electric heater 220 is received within the aerosol-forming substrate.

The remainder of the aerosol-generating device 200, including the head conductive assembly 46, is identical to the aerosol-generating device 10 of FIG. 1.

The invention claimed is:

1. An aerosol-generating device, comprising:
   an aerosol generator configured to generate an aerosol from an aerosol-forming substrate;
   a power supply;
   a circuit board comprising a control circuit configured to control a supply of power from the power supply to the aerosol generator; and
   a heat conductive assembly comprising a first end in thermal contact with the circuit board and a second end spaced apart from the circuit board,
   wherein the circuit board is a first circuit board, wherein the aerosol-generating device further comprises a second circuit board, and wherein the first end of the heat conductive assembly is in thermal contact with the second circuit board, and
   wherein the second circuit board at least partially overlies the first circuit board, wherein the second circuit board is spaced apart from the first circuit board, and wherein the first end of the heat conductive assembly is positioned between the first circuit board and the second circuit board.

2. The aerosol-generating device according to claim 1, wherein the second end of the heat conductive assembly is in thermal contact with the power supply.

3. The aerosol-generating device according to claim 1,
   wherein the heat conductive assembly further comprises a heat conductive frame defining the second end of the heat conductive assembly, and
   wherein the power supply is positioned at least partially within the heat conductive frame.

4. The aerosol-generating device according to claim 1,
   wherein the heat conductive assembly further comprises at least one transverse member at the first end of the heat conductive assembly, and wherein a portion of the at least one transverse member is positioned within a slot defined by the circuit board.

5. The aerosol-generating device according to claim 1, wherein the heat conductive assembly further comprises a heat conductive frame defining the second end of the heat conductive assembly,
wherein the power supply is positioned at least partially within the heat conductive frame,
wherein the heat conductive assembly further comprises at least one transverse member at the first end of the heat conductive assembly,
wherein a portion of the at least one transverse member is positioned within a slot defined by the circuit board, and
wherein the heat conductive assembly comprises at least one longitudinal arm extending between the at least one transverse member and the heat conductive frame.

6. The aerosol-generating device according to claim 4, wherein the slot defined by the circuit board is a first slot, wherein the circuit board further defines a second slot, wherein the at least one transverse member comprises a first transverse member having a first portion positioned within the first slot, and
wherein the at least one transverse member further comprises a second transverse member having a second portion positioned within the second slot.

7. The aerosol-generating device according to claim 3, wherein at least a portion of the at least one transverse member is positioned within a slot defined by the second circuit board.

8. The aerosol-generating device according to claim 6, wherein the second circuit board defines a third slot, and wherein the second transverse member has a third portion positioned within the third slot.

9. The aerosol-generating device according to claim 8, wherein first transverse member is in thermal contact with the first circuit board only.

10. The aerosol-generating device according to claim 1, further comprising at least one additional electrical component,
wherein the at least one additional electrical component comprises at least one of a charging connector, a user input device, and a feedback device, and
wherein the at least one additional electrical component is electrically connected to the second circuit board.

11. The aerosol-generating device according to claim 1, further comprising an inner housing,
wherein the power supply is positioned within the inner housing, and
wherein a portion of the inner housing is overmolded over at least a part of the second end of the heat conductive assembly.

12. The aerosol-generating device according to claim 1, further comprising an inner housing,
wherein the power supply is positioned within the inner housing, and
wherein at least a part of the second end of the heat conductive assembly overlies a portion of the inner housing.

13. The aerosol-generating device according to claim 1, wherein the aerosol generator comprises an inductive heating arrangement.

* * * * *